(12) United States Patent
Stad et al.

(10) Patent No.: US 7,867,237 B2
(45) Date of Patent: Jan. 11, 2011

(54) ARTHROPLASTY REVISION DEVICE AND METHOD

(75) Inventors: Shawn D. Stad, Fall River, MA (US); Mark Gracia, Rochester, MA (US)

(73) Assignee: DePuy Spine, Inc., Raynham, MA (US)

( * ) Notice: Subject to any disclaimer, the term of this patent is extended or adjusted under 35 U.S.C. 154(b) by 749 days.

(21) Appl. No.: 11/263,603

(22) Filed: Oct. 31, 2005

(65) Prior Publication Data
US 2007/0100347 A1  May 3, 2007

(51) Int. Cl.
A61B 17/58 (2006.01)
A61B 17/60 (2006.01)
A61F 2/00 (2006.01)

(52) U.S. Cl. .......................................... 606/90; 606/99
(58) Field of Classification Search ................ 606/198, 606/90, 57, 105, 99, 104, 86 A, 86 B, 205–208
See application file for complete search history.

(56) References Cited

U.S. PATENT DOCUMENTS

| | | | |
|---|---|---|---|
| 3,486,505 A | 12/1969 | Morrison | |
| 4,803,983 A * | 2/1989 | Siegel | 606/151 |
| 4,898,161 A | 2/1990 | Grundei | |
| 4,944,744 A | 7/1990 | Ray | |
| 4,997,432 A * | 3/1991 | Keller | 623/17.11 |
| 5,015,247 A | 5/1991 | Michelson | |
| 5,304,119 A | 4/1994 | Balaban et al. | |
| 5,401,269 A * | 3/1995 | Buttner-Janz et al. | 623/17.15 |
| 5,431,658 A | 7/1995 | Moskovich | |
| 5,484,437 A | 1/1996 | Michelson | |
| 5,505,732 A | 4/1996 | Michelson | |

(Continued)

FOREIGN PATENT DOCUMENTS

EP  1306064  5/2003

(Continued)

OTHER PUBLICATIONS

Capasso, G. Velotti A.. and Auzino, G., "Mechanical Behavior of Two Types of Vertebral Distractors Submitted to Compression-Flexion Tests," *Ital J. Orthop Traumatol.* 13(1):121-6 (1987).

(Continued)

*Primary Examiner*—Todd E Manahan
*Assistant Examiner*—Erin Colello
(74) *Attorney, Agent, or Firm*—Nutter McClennen & Fish LLP (57) ABSTRACT

A surgical instrument for revising/removing an artificial disc or removing/replacing a core of an artificial disc includes a pair of tips, each tip having a pair of tines and a stop defining a proximal end of each tine. The stop of at least one tip is abutted against an interior surface of an implanted endplate of an artificial disc, whereby tines of the tip can support the artificial disc. The tip is separated from another, opposing tip, whereby opposing implanted endplates, each of which is supported by pairs of tines of a tip, are separated, thereby distracting vertebrae between which the endplates are implanted. Upon distracting the disc space, the core can be revised or removed from between the endplates of the artificial disc. Following core removal, the endplates of the artificial disc are revised (repositioned), removed or replaced.

19 Claims, 10 Drawing Sheets

U.S. PATENT DOCUMENTS

| | | | |
|---|---|---|---|
| 5,722,977 A | 3/1998 | Wilhelmy | |
| 5,741,253 A | 4/1998 | Michelson | |
| 5,885,299 A | 3/1999 | Winslow et al. | |
| 5,951,564 A | 9/1999 | Schroder et al. | |
| 6,042,582 A | 3/2000 | Ray | |
| 6,063,088 A | 5/2000 | Winslow | |
| 6,083,225 A | 7/2000 | Winslow et al. | |
| 6,113,602 A | 9/2000 | Sand | |
| 6,159,215 A | 12/2000 | Urbahns et al. | |
| 6,200,322 B1 | 3/2001 | Branch et al. | |
| 6,261,296 B1* | 7/2001 | Aebi et al. | 606/90 |
| 6,267,763 B1 | 7/2001 | Castro | |
| 6,277,122 B1 | 8/2001 | McGahan et al. | |
| 6,436,119 B1 | 8/2002 | Erb et al. | |
| 6,440,142 B1 | 8/2002 | Ralph et al. | |
| 6,520,967 B1 | 2/2003 | Cauthen | |
| 6,551,316 B1* | 4/2003 | Rinner et al. | 606/57 |
| 6,719,760 B2 | 4/2003 | Dorchak et al. | |
| 6,575,981 B1 | 6/2003 | Boyd et al. | |
| 6,582,437 B2 | 6/2003 | Dorchak et al. | |
| 6,589,247 B2 | 7/2003 | McGahan et al. | |
| 6,599,291 B1 | 7/2003 | Foley et al. | |
| 6,648,888 B1 | 11/2003 | Shluzas | |
| 6,648,895 B2 | 11/2003 | Burkus et al. | |
| 6,663,638 B2 | 12/2003 | Ralph et al. | |
| 6,712,825 B2* | 3/2004 | Aebi et al. | 606/90 |
| 6,743,234 B2 | 6/2004 | Burkus et al. | |
| 6,814,737 B2 | 11/2004 | Cauthen | |
| 6,936,071 B1* | 8/2005 | Marnay et al. | 623/17.15 |
| 7,081,118 B2* | 7/2006 | Weber et al. | 606/90 |
| 7,083,649 B2* | 8/2006 | Zucherman et al. | 623/17.11 |
| 7,169,153 B2* | 1/2007 | Keller | 606/99 |
| 7,235,101 B2* | 6/2007 | Berry et al. | 623/17.11 |
| 7,273,496 B2* | 9/2007 | Mitchell | 623/17.14 |
| 7,575,576 B2* | 8/2009 | Zubok et al. | 606/90 |
| 7,585,326 B2* | 9/2009 | de Villiers et al. | 623/17.15 |
| 7,618,444 B2* | 11/2009 | Shluzas | 606/279 |
| 2001/0029377 A1* | 10/2001 | Aebi et al. | 606/105 |
| 2001/0031968 A1 | 10/2001 | Dorchak et al. | |
| 2001/0031969 A1 | 10/2001 | Aebi et al. | |
| 2002/0123754 A1 | 9/2002 | Holmes et al. | |
| 2002/0143343 A1 | 10/2002 | Castro | |
| 2002/0198532 A1 | 12/2002 | Michelson | |
| 2003/0069586 A1 | 4/2003 | Errico et al. | |
| 2003/0078590 A1 | 4/2003 | Errico et al. | |
| 2003/0125739 A1* | 7/2003 | Bagga et al. | 606/61 |
| 2003/0149438 A1 | 8/2003 | Nichols et al. | |
| 2003/0212404 A1 | 11/2003 | Dorchak et al. | |
| 2003/0225416 A1* | 12/2003 | Bonvallet et al. | 606/105 |
| 2004/0039397 A1* | 2/2004 | Weber et al. | 606/90 |
| 2004/0078079 A1 | 4/2004 | Foley | |
| 2004/0097932 A1* | 5/2004 | Ray et al. | 606/61 |
| 2004/0098129 A1 | 5/2004 | Lin | |
| 2004/0102790 A1 | 5/2004 | Ralph et al. | |
| 2004/0106927 A1 | 6/2004 | Ruffner et al. | |
| 2004/0117019 A1 | 6/2004 | Trieu et al. | |
| 2004/0167535 A1 | 8/2004 | Errico et al. | |
| 2004/0167536 A1 | 8/2004 | Errico et al. | |
| 2004/0172037 A1 | 9/2004 | Dorchak et al. | |
| 2004/0176764 A1* | 9/2004 | Dant | 606/61 |
| 2004/0199163 A1 | 10/2004 | Whittaker et al. | |
| 2004/0225295 A1* | 11/2004 | Zubok et al. | 606/90 |
| 2005/0010213 A1 | 1/2005 | Stad et al. | |
| 2005/0027300 A1 | 2/2005 | Hawkins et al. | |
| 2005/0033305 A1* | 2/2005 | Schultz | 606/99 |
| 2005/0043741 A1 | 2/2005 | Michelson | |
| 2005/0075644 A1 | 4/2005 | DiPoto et al. | |
| 2005/0119665 A1* | 6/2005 | Keller | 606/99 |
| 2005/0143747 A1* | 6/2005 | Zubok et al. | 606/90 |
| 2005/0159756 A1 | 7/2005 | Ray | |
| 2005/0165408 A1 | 7/2005 | Puno et al. | |
| 2006/0030856 A1* | 2/2006 | Drewry et al. | 606/90 |
| 2006/0030862 A1* | 2/2006 | De Villiers et al. | 606/99 |
| 2006/0074432 A1* | 4/2006 | Stad et al. | 606/90 |
| 2006/0116768 A1* | 6/2006 | Krueger et al. | 623/17.14 |
| 2006/0287728 A1* | 12/2006 | Mokhtar et al. | 623/17.14 |
| 2007/0123903 A1 | 5/2007 | Raymond et al. | |
| 2007/0123904 A1 | 5/2007 | Stad et al. | |

FOREIGN PATENT DOCUMENTS

| | | |
|---|---|---|
| WO | WO-01/19295 | 3/2001 |
| WO | WO-02/071986 | 9/2002 |

OTHER PUBLICATIONS

Rutsky, V.V. and Valkav, A.N., "Designing a dynamic spinal distractor," *Med Tekh*. 4:29-32 (1995).

Demetropoulas, C.K., Truumees, E., Herkowitz, H.N. and Yang, K.H., "Development and calivration of a load sensing cervical distractor capable of withstanding autoclave sterilization," *Med Eng Phys*. 27(4):343-6 (2005).

Australian Examiner's report in AU Pat. App. No. 2006309102 issued Jul. 22, 2009 (6 pages).

International Search Report in PCT/US2006/041402 issued Mar. 1, 2007.

European Examination Report in EP06823529.7 issued May 31, 2010 (11 pages).

* cited by examiner

ARTHROPLASTY REVISION DEVICE AND METHOD

BACKGROUND OF THE INVENTION

Arthroplasty is becoming significantly more prevalent as a surgical procedure to treat injury and disease. Of particular importance is the use of artificial discs to replace vertebral discs as functioning artificial joints.

Instrumentation employed to conduct surgical techniques that implant artificial discs still are of limited variety and generally do not permit modification subsequent to completion of the procedure without radical reconstruction and a significant likelihood of additional tissue damage. Artificial discs typically include two endplates and a core between endplates. The core permits movement of the endplates relative to each other, thereby simulating the function of the intervertebral disc that it replaces. Artificial discs can be implanted as complete assemblies, or, alternatively, endplates of an artificial disc can be inserted first, followed by placement of a core between the endplates. As in any surgical implantation, the initial placement may not be optimal. In such an instance, the surgeon typically is left with the option of leaving the implant in a sub-optimal position or removing it, and replacing the implant in a more optimal position. During the process, further traumatization of the surrounding tissue can occur. Therefore, a need exists for a device and a method that significantly eliminates or reduces the above-referenced problems.

SUMMARY OF THE INVENTION

The invention is directed to a surgical instrument and a method for revising/removing an artificial disc or removing/replacing a core of an artificial disc.

In one embodiment, a surgical instrument of the invention includes a pair of tips, each tip having a pair of tines and a stop defining a proximal end of each tine. In one embodiment, the stop of each tip extends between the tines of the tip. The tines of each tip also can essentially match the tines of the other tip. In one embodiment, the tines of each tip have a flat surface, and the flat surface of the tines of each tip are parallel. Alternatively, the tines of each tip can have surfaces that complement surfaces of the tines of the other tip. In one such embodiment, each tip includes a base portion, wherein the tines of each tip extend from the base portion. Also, the base portion of each tip can include a surface, at least a portion of which complements at least a portion of a surface of a base portion of the other tip. In one embodiment, the complementary surfaces of the base portion are continuous with the complementary surface of at least one tine of each tip. The continuous complementing surfaces of the tips can partition the remaining portion of the base of each tip when the complementary surfaces of the tips are in contact with each other.

In one embodiment, the surgical instrument includes a forceps portion. In one embodiment, the forceps portion is a double-action forceps. In another embodiment, the forceps portion is a parallel-action forceps. The tips can be releasable from the forceps portion. In one embodiment, at least one of the tips is releasable by activation of a spring-loaded clip that releasably couples the tip to the forceps portion. In a specific embodiment, a major axis of the tines extends at an oblique angle to a major axis of the forceps portion. The base of at least one of the tips can define a chamfered recess having a major axis essentially parallel to a major axis of the tines of the tip. In a specific embodiment, both tips can define a chamfered recess, wherein the chamfered recesses are opposed to each other when the tips are coupled to the forceps portion. In a particular embodiment, the continuous step of at least one tip is chamfered.

A method of revising a position of an artificial disc or of implanting a core of an artificial disc includes abutting the stop of at least one tip against an outer surface of an implanted endplate of the artificial disc, whereby tines of the tip can support the artificial disc. The tip is then separated from another, opposing tip, whereby opposing implanted endplates, each of which is supported by a pair of tines of a tip, are separated, thereby distracting vertebrae between which the endplates are implanted. The core between the endplates can then be removed and replaced by one that is more appropriately sized (e.g., height of the core), or the core can be removed so that the endplates can be removed and easily repositioned (revised) or replaced. In a specific embodiment, the stops of each pair of tips abuts each of a pair of opposing implanted endplates. In one embodiment, the tips are abutted against the endplates simultaneously. The tips can be abutted against the endplates while the tips are in a nested position. In one embodiment, the tips are separated from each other by actuating nonparallel-action forceps to which the tips are attached or of which they are a component. In another embodiment, the tips are separated from each other by actuating a parallel-action forceps to which the tips are attached or of which they are a component. The method can further include the step of releasing the forceps, whereby the endplates each rest against the core.

The present invention has many advantages. For example, the apparatus and method of the invention permit revision or implantation of a core of an artificial disc without disturbing seating of implanted endplates of the artificial disc. Accordingly, the surgeon can conduct any necessary iterative procedure that may be required to optimally place a core between implanted endplates of an artificial disc. Further, implanted endplates can be distracted with minimal movement, thereby also minimizing trauma to adjacent tissue. Also, abutting stops of the tines of each tip against an endplate enables the apparatus to be freely manipulated by the surgeon without significant risk of injury by incidental contact of the tines, such as by contact of the tines to nerve tissue.

DETAILED DESCRIPTION OF THE INVENTION

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Figure 1A:
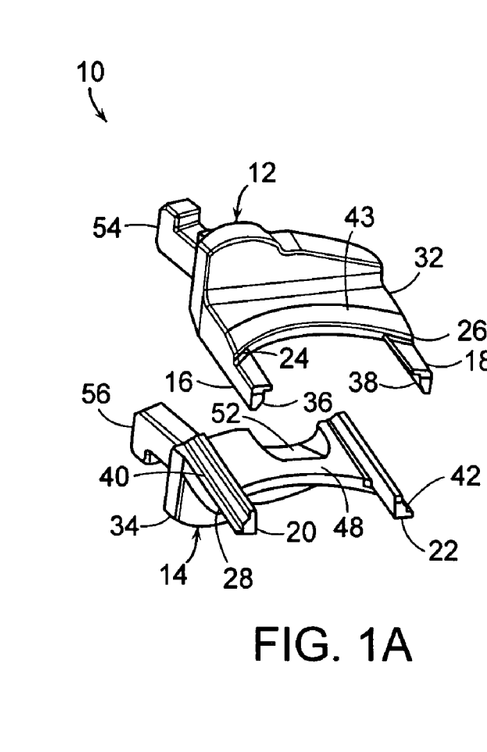
FIG. 1A is a perspective view of a pair of tips of a surgical instrument of the invention.
Figure 1B:
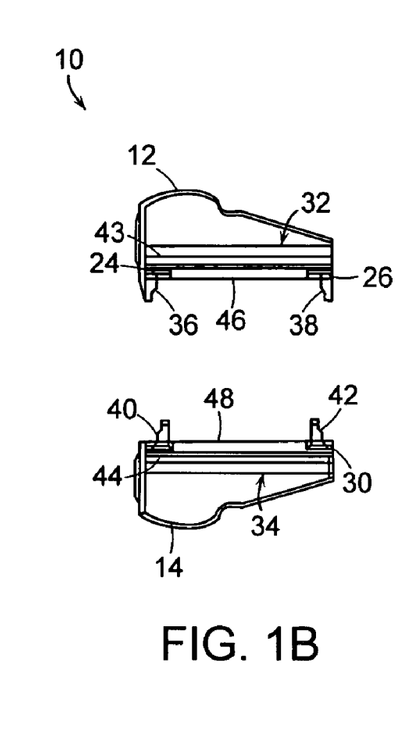
FIG. 1B is an end view of the pair of tips shown in FIG. 1A.
Figure 1C:
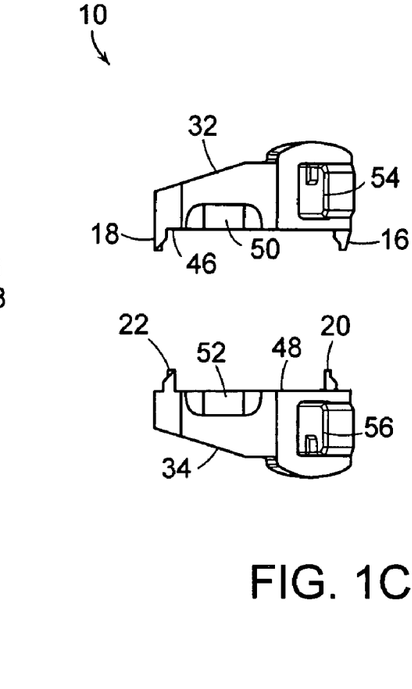
FIG. 1C is an opposing end view of the pair of tips shown in FIG. 1A.

The invention generally is directed to a surgical instrument and method for revising the position of, or implanting a core between, implanted endplates of an artificial disc. FIGS. 1A, 1B and 1C represent perspective and opposing end views of pair of tips 10 of the surgical instrument of the invention in a distracted position. Tip 12 and opposing tip 14 include pairs of tines 16, 18 and 20, 22, respectively. Tines 16, 18 of tip 12 and tines 20, 22 of opposing tip 14 are each defined by stops 24, 26 and stops 28, 30, respectively.

Tip 12 and opposing tip 14 include base 32 and base 34, respectively. As shown in FIG. 1A, stops 24, 26 of tip 12 are continuous along base 32. In corresponding manner, stops 28, 30 define a continuous surface along base 34 of opposing tip 14. Tines 16, 18 of tip 12 and tines 20, 22 of opposing tip 14, along with a portion of base 32 and base 34, define complementary surfaces 36, 38 of tip 12, and complementary surfaces 40, 42 of opposing tip 14. Specifically, complementary surface 36 nests with complementary surface 40 and complementary surface 38 nests with complementary surface 42. As shown in FIG. 1B, tip 12 and opposing tip 14 also include chamfered surfaces 43, 44, at base 32 and base 34, respectively. As shown in FIG. 1C, tips 12, 14 also include recessed portions 46, 48, which define chamfered recesses 50, 52, respectively. Chamfered recesses 50, 52 oppose each other when complementary surfaces 36, 40 and 38, 42 are nested. Chamfered recesses 50, 52 each include a major axis that is essentially parallel to a plane extending through at least one tine of a respective tip. Chamfered recesses 50, 52 are intended to allow access to space between tines during core removal/replacement.

Modular connectors 54, 56 extend from base 32 and base 34, respectively. A major axis of each of modular connectors 54, 56 extends through a major axis of at least one tine and a respective tip at an oblique angle. Preferably, the oblique angle is in a range of between about 1 degree and about 20 degrees. In a particularly preferred embodiment, the oblique angle is 15 degrees. In the alternative, a major axis of the tines is parallel to the major axis of the forceps, or distraction instrument.

Figure 2A:
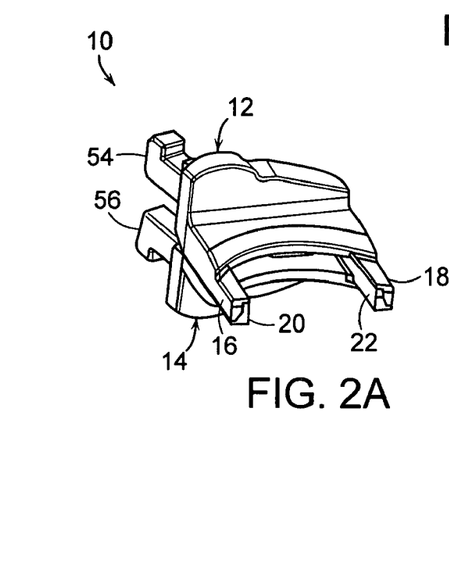
FIG. 2A is a perspective view of FIGS. 1A-1C in a nearly-nested position.
Figure 2B:
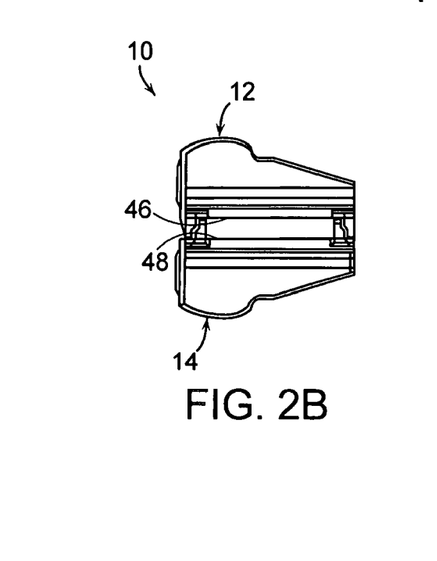
FIG. 2B is an end view of the pair of tips in the nearly-nested position shown in FIG. 2A.
Figure 2C:
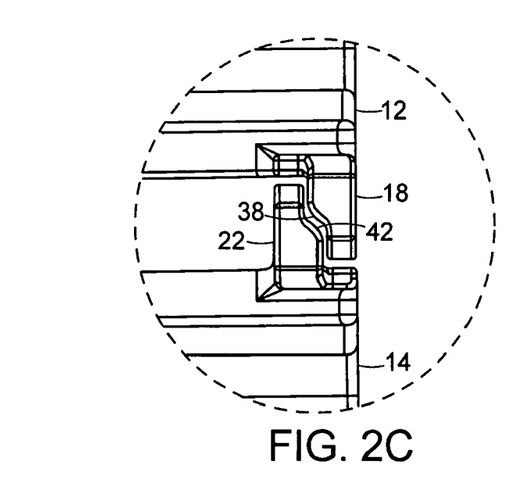
FIG. 2C is a detail of the end view of FIG. 2B, showing the tines of the pair of tips nearly nested.
Figure 2D:
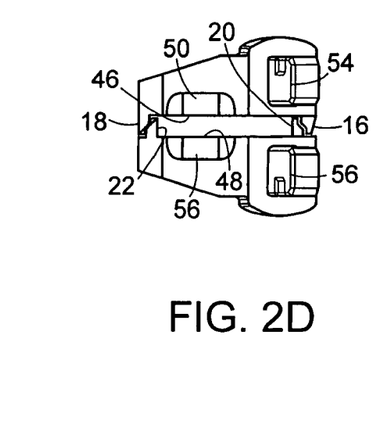
FIG. 2D is an opposing end view of the pair of tips shown in FIG. 2A in the nearly-nested position.
Figure 2E:
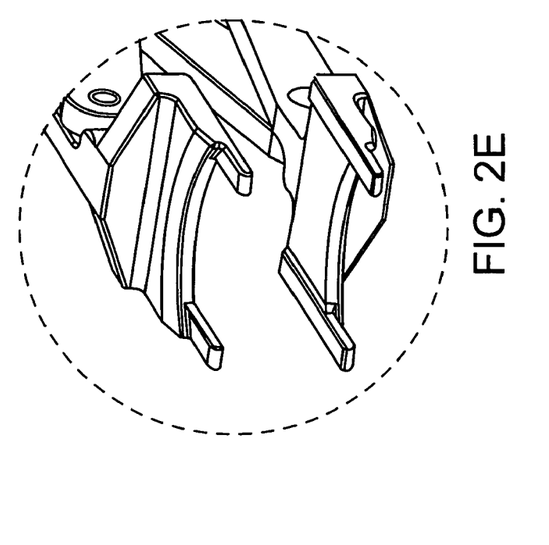
FIG. 2E is an alternative embodiment of the surgical instrument of the invention wherein the pair of tips abut each other at flat surfaces.

FIGS. 2A, 2B and 2D represent perspective and opposing end views of the surgical instrument of the invention shown in FIGS. 1A-1C in a nearly-nested or nearly-reduced position. Tip 12 and opposing tip 14 are nearly-nested, because, as can be seen in FIG. 2C, which is a detail of FIG. 2B, complementary surfaces 38, 42 of tines 18, 22, respectively, are not in contact, but are in close proximate relation to each other. Upon contact, tip 12 and opposing tip 14 would be in a nested position. It is to be understood, however, that as an alternative to complementary surfaces, tines of opposing tips can abut without being complementary. In one embodiment, the tines of opposing tips can abut in a retracted position at continuous flat surfaces of the tines, as shown in FIG. 2E (in a distracted position).

Figure 3A:
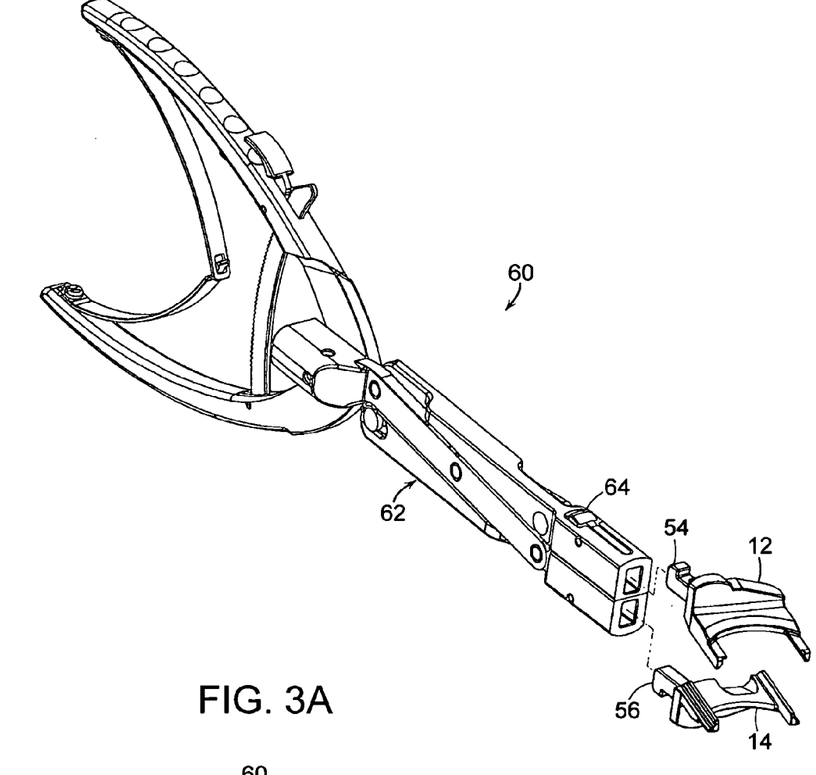
FIG. 3A is a perspective view of the pair of tips of FIGS. 1A-1C and 2A-2D in combination with a parallel-action forceps in a retraction position and of the relation of the pair of tips to the parallel-action forceps upon assembly.
Figure 3B:
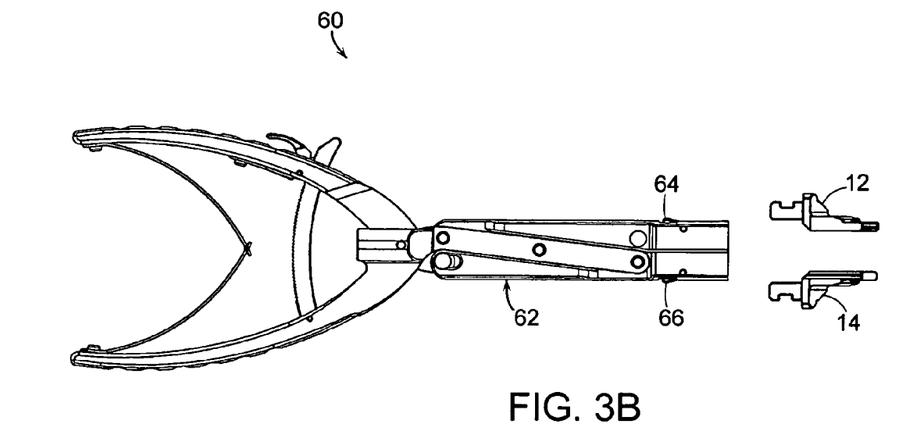
FIG. 3B is a side view of the embodiment shown in FIG. 3A.
Figure 3C:
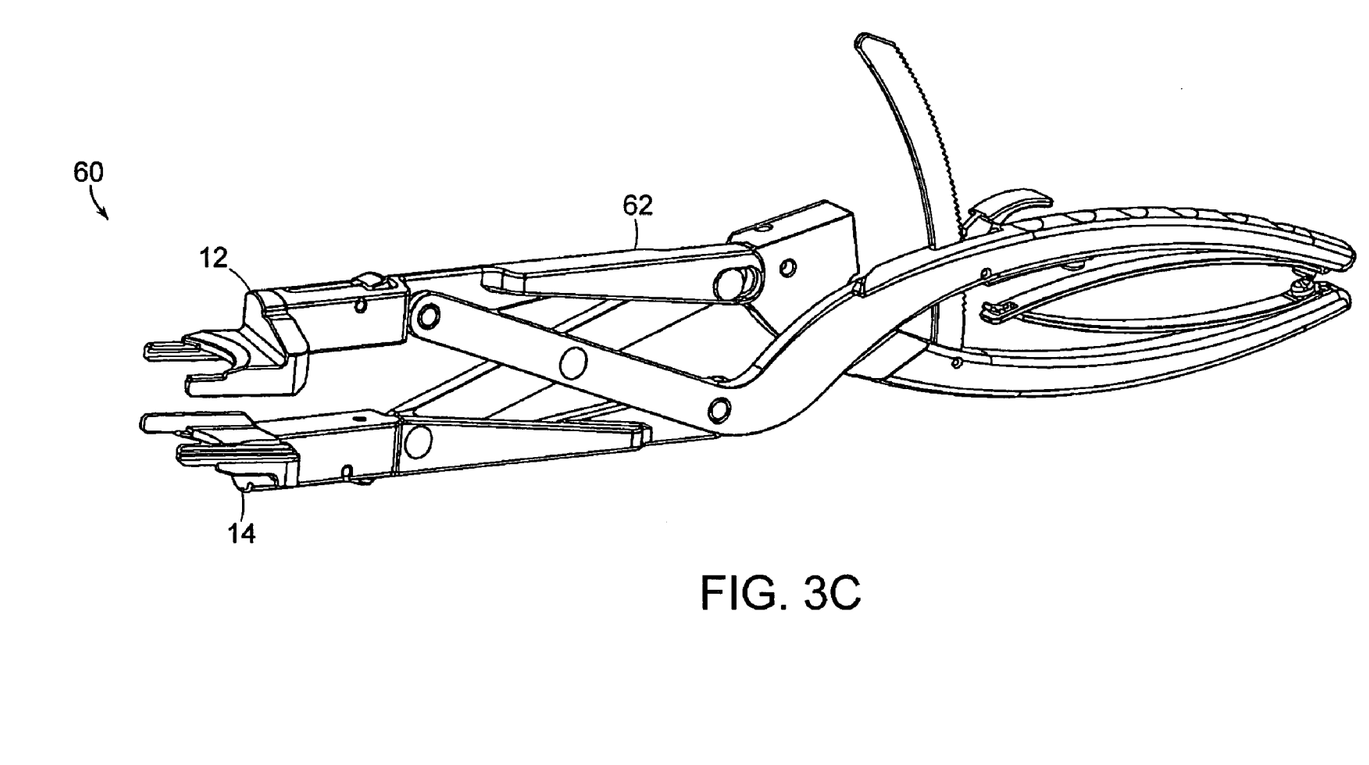
FIG. 3C is a perspective view of the embodiment of FIGS. 3A and 3B in a distracted position.
Figure 3D:
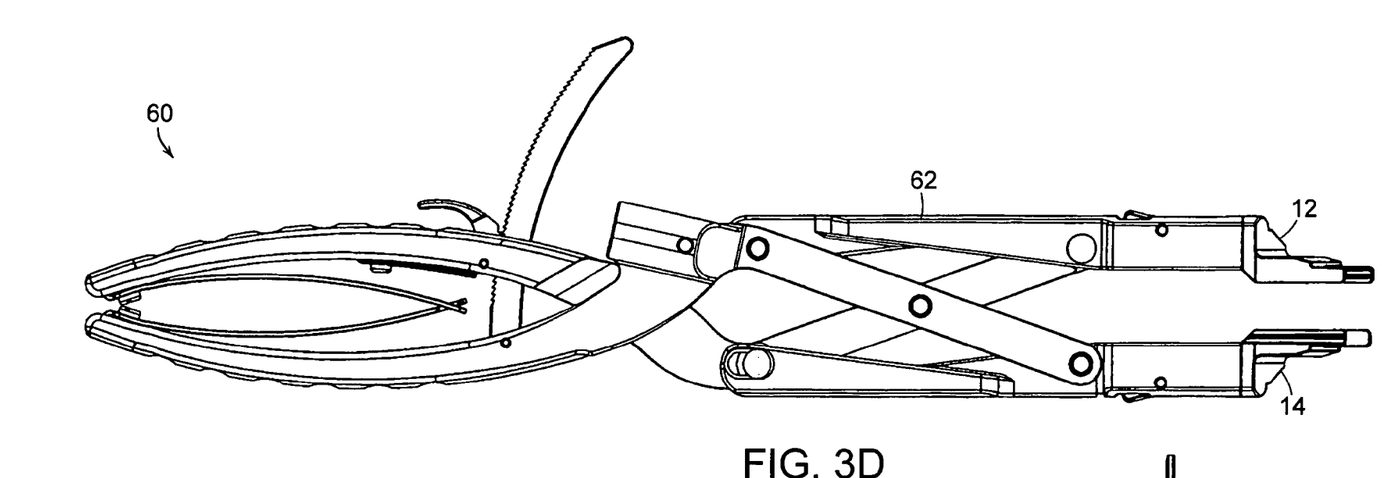
FIG. 3D is a side view of the embodiment of FIG. 3C in the distracted position.
Figure 3E:
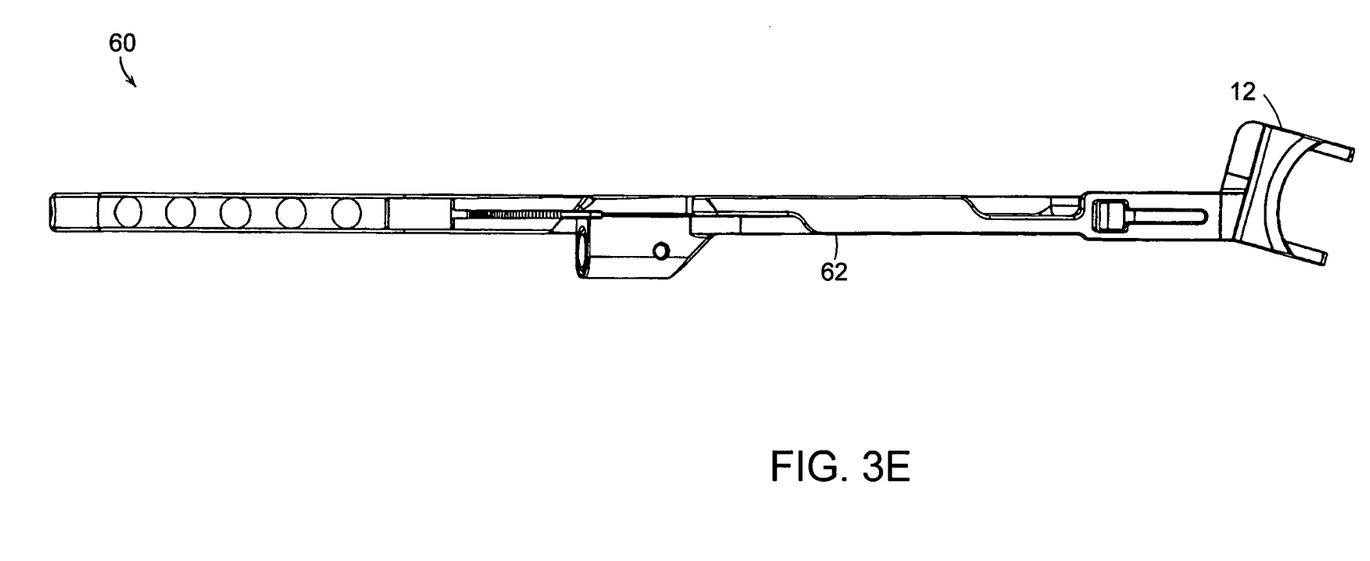
FIG. 3E is a plan view of the embodiment of FIG. 3C.
Figure 3F:
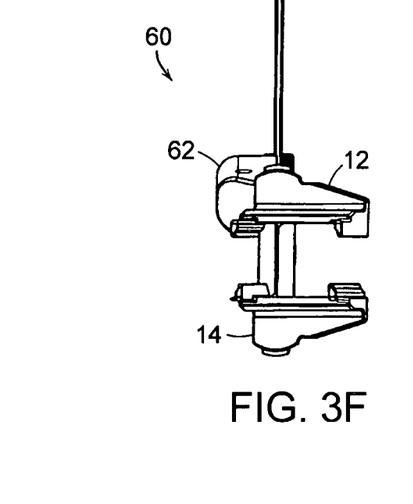
FIG. 3F is an end view of the embodiment of FIG. 3C.
Figure 4:
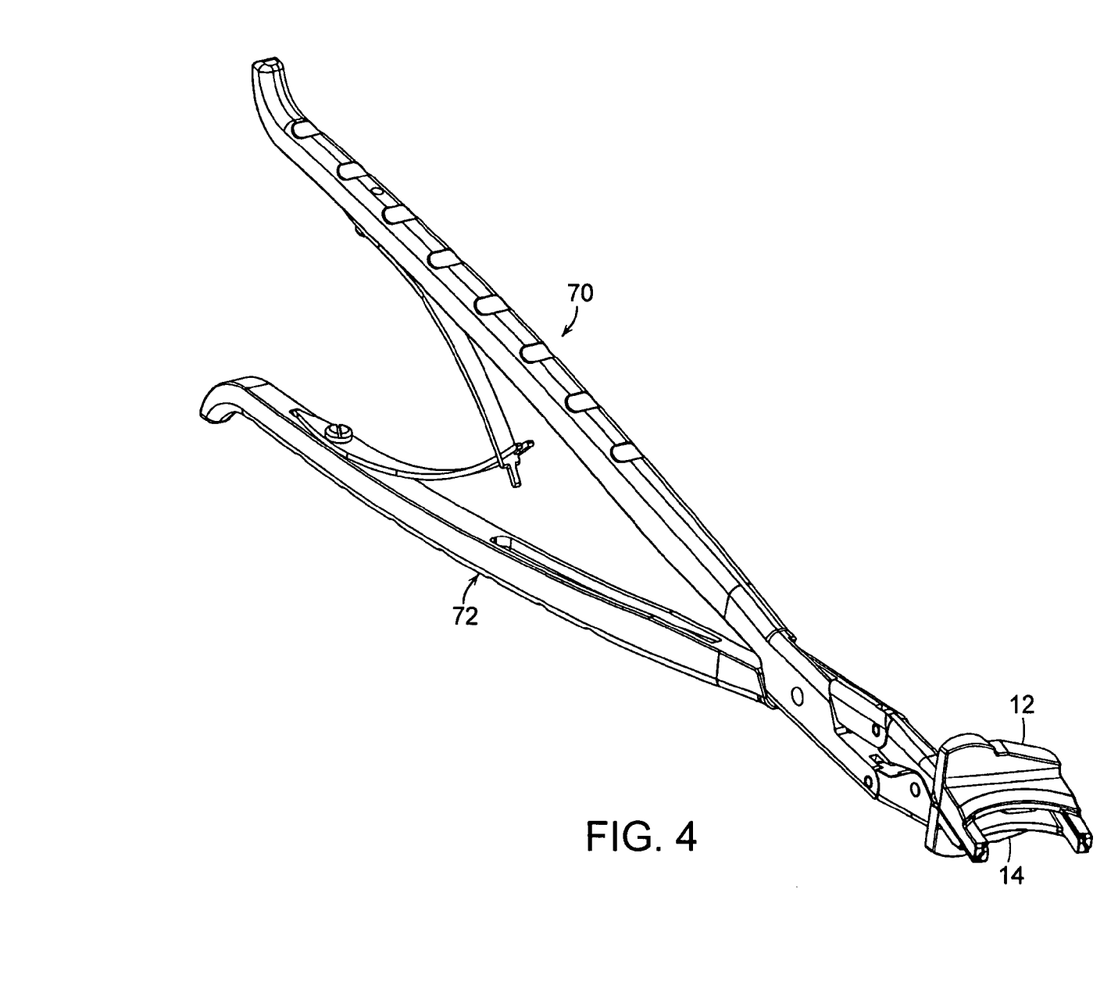
FIG. 4 is a perspective view of the pair of tips of FIGS. 1A-1C and 2A-2D in combination with a nonparallel-action forceps in a retraction position.
Figure 5A:
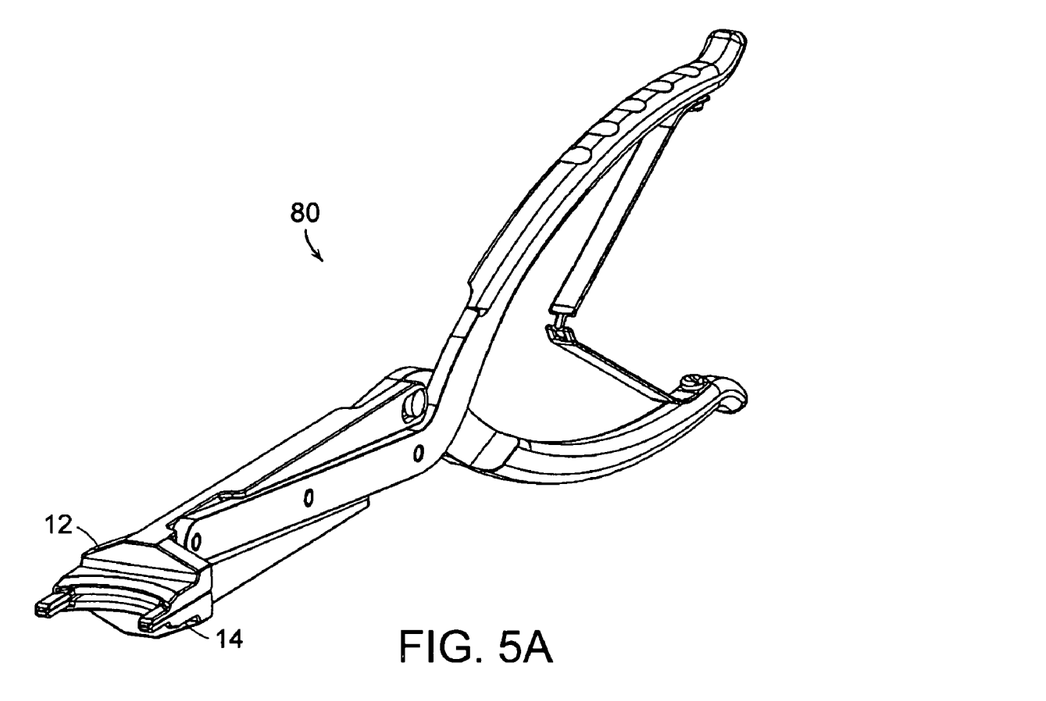
FIG. 5A is a perspective view of the invention in a retracted position where tips are non-modular components of parallel action forceps.
Figures 5B, 5C:
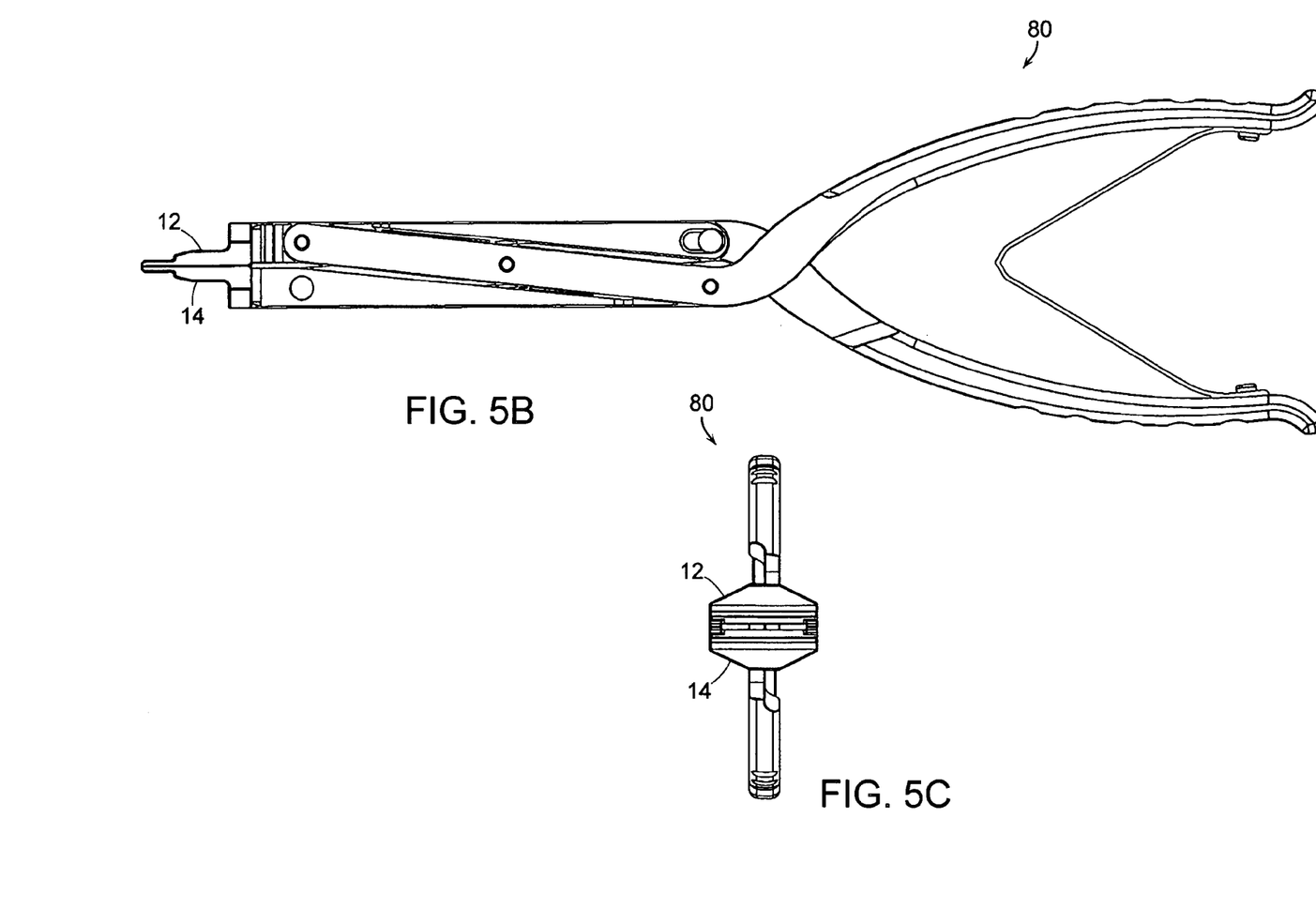
FIG. 5B is a side view of the embodiment shown in FIG. 5A.
FIG. 5C is an end view of the embodiment shown in FIG. 5A.
Figure 5D:
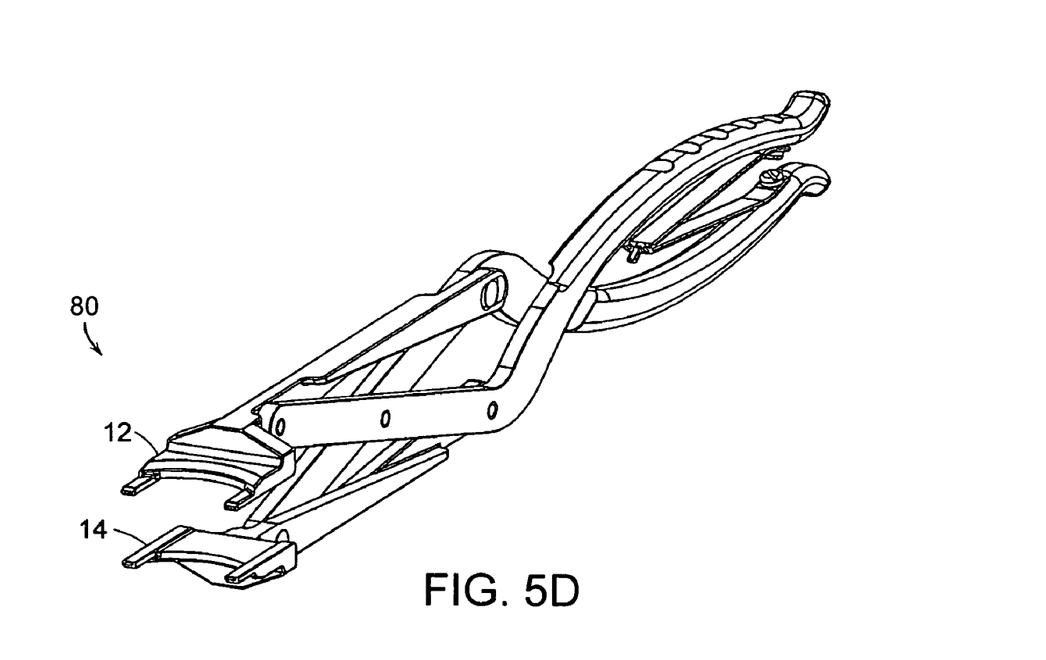
FIG. 5D is a perspective view of the embodiment of FIG. 5A in a distracted position.
Figure 5E:
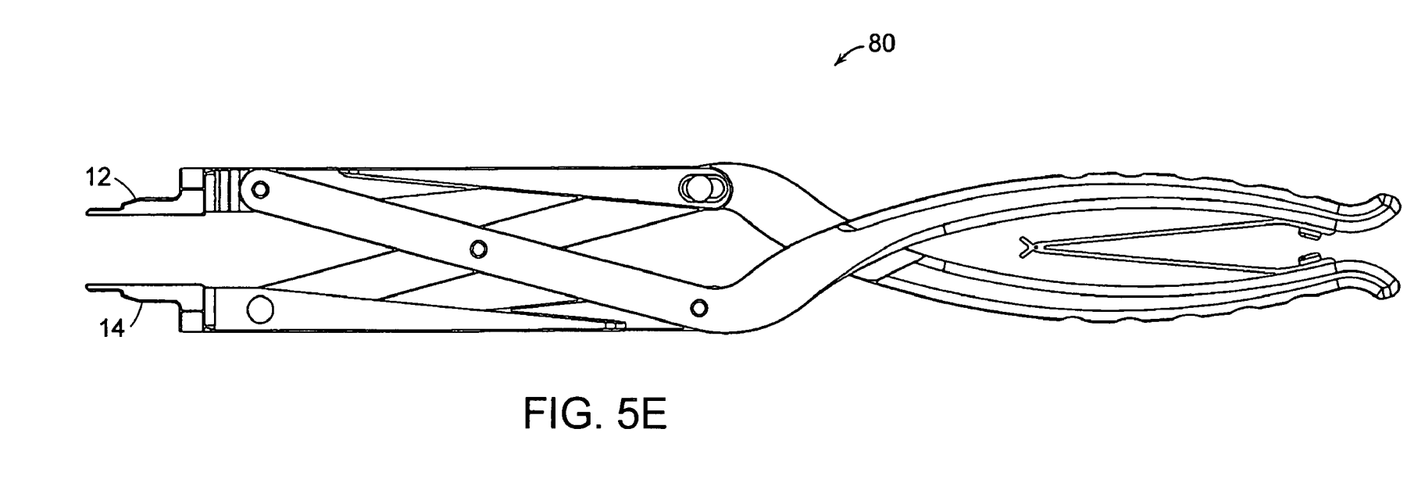
FIG. 5E is a side view of the embodiment of FIG. 5D.
Figure 5F:
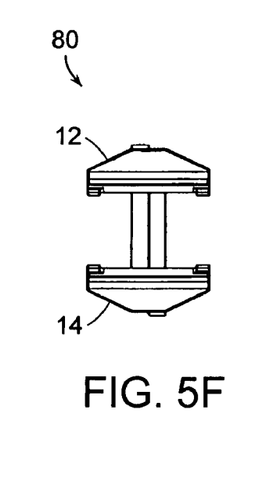
FIG. 5F is an end view of the embodiment of FIG. 5D.

FIGS. 3A and 3B represent, respectively, perspective and side views of surgical instrument 60 of the invention that includes parallel-action forceps 62 in combination with tip 12 and opposing tip 14 of FIGS. 1A-1C and FIGS. 2A-2D. Parallel-action forceps 62 can be any suitable parallel-action forceps, such as is described in U.S. Pat. No. 5,122,130, issued to Keller on Jun. 16, 1992, the entire teachings of which are incorporated herein by reference. Tips 12 and 14 can be modular, whereby they are releasable from another component of a surgical instrument. As shown in FIGS. 3A and 3B, tip 12 and opposing tip 14 are compatible for coupling with parallel-action forceps 62 at modular connectors 54, 56. Modular connectors link with the parallel-action forceps with spring-loaded clips 64, 66, respectively. It is to be understood, however, that any suitable coupling mechanism could be employed, such as described in U.S. Ser. No. 10/616,506, filed Jul. 8, 2003, and U.S. Ser. No. 10/959,598, filed Oct. 6, 2004, the entire teachings of both of which are incorporated herein by reference. FIGS. 3A and 3B represent surgical instrument 60 in a reduced position. FIGS. 3C, 3D, 3E and 3F represent surgical instrument 60 in a distracted position, with tip 12 and opposing tip 14 assembled with parallel-action forceps 62. Alternatively, tip 12 and opposing tip 14 can be a component of or suitably connected such as by a modular connection as described, for example, above, to a nonparallel-action forceps as opposed to a parallel-action forceps. A representative example of a nonparallel-action forceps is shown in FIG. 4, wherein surgical instrument 70 includes nonparallel-action forceps 72 coupled to tip 12 and opposing tip 14. In another embodiment, tip 12 and tip 14 can be non-modular components of parallel action or non-parallel action forceps. FIG. 5A is a perspective view of tip 12 and tip 14 as components of parallel action forceps 80 arranged as a non-modular embodiment in a retracted position. FIGS. 5B and 5C are side and end views, respectively, of the non-modular embodiment of FIG. 5A. FIGS. 5D, 5E and 5F are perspective, side and end views, respectively, of the embodiment of FIG. 5A in a distracted position.

In a method of the invention, the size of a core of an artificial disc is revised, or the core of an artificial disc is implanted, by abutting the stop or stops of at least one tip of the invention against an interior surface of an implanted endplate of an artificial disc, whereby tines of the tip can support the artificial disc. The tip is separated from another opposing tip, whereby opposing implanted endplates, each of which is supported by pairs of tines of a tip, are separated, thereby distracting vertebrae between which the endplates are implanted. Preferably, the stops and the tines of each tip comport with each endplate, whereby the force of distraction of the vertebrae is born, at least substantially, if not entirely, by the endplates, rather than by the force of direct contact between the vertebrae and the tines. Upon sufficient distraction of the vertebrae, the core between the artificial disc can be revised or the core can be removed, implanted, or both, between the endplates of the artificial disc. Preferably, the tips are abutted against the endplates while the tips are in a nested position. Actuation of the nonparallel-action forceps or parallel-action forceps moves the forceps from a reduced position, such as in shown in FIGS. 3A and 3B, in the case of parallel-action forceps, to a distracted position, such as is shown in FIGS. 3C through 3F, thereby distracting vertebrae adjacent to implanted endplates of an artificial disc. In another embodiment of the method of the invention, the core can be removed, followed by removal of the pair of tips from between the endplates, and revision (repositioning), removal and/or replacement of the endplates of the artificial disc. The endplates can then be distracted again by use of the pair of tips, as described above, and a core, of either the same or a different size can be implanted between the endplates. The pair of tips is then removed by releasing the forceps, and the operation is completed.

While this invention has been particularly shown and described with reference to various embodiments thereof, it will be understood by those skilled in the art that various changes in form and details may be made therein without departing from the scope of the invention encompassed by the appended claims.

What is claimed is:

1. A surgical instrument, comprising a pair of tips configured to distract vertebrae, each tip having a pair of tines configured to support a core implant, a stop defining a continuous surface along a proximal end of each tine and configured to limit proximal movement of a core implant seated between the pair of tips, and a recessed portion recessed from the pair of tines and having a recess formed in a proximal portion of the recessed portion such that an entirety of the recess is located proximal to the continuous surface of the stop,
    wherein the pair of tines on one of the pair of tips nests within the pair of tines on the other one of the pair of tips,
    wherein facing planar surfaces of the recessed portions do not contact one another when the pair of tines on one of the pair of tips nests within the pair of tines on the other one of the pair of tips, and
    wherein the recesses formed in the tips face each other and are opposed to one another such that the recesses define a space that allows access to a space between the tines.

2. The surgical instrument of claim 1, wherein the stop of each tip extends between the tines of the tip.

3. The surgical instrument of claim 2, wherein the tines of each tip essentially match the tines of the other tip.

4. The surgical instrument of claim 3, wherein the tines of each tip have a flat surface, and wherein the flat surfaces of the tines of each tip are parallel.

5. The surgical instrument of claim 3, wherein the tines of each tip have surfaces that complement surfaces of the tines of the other tip.

6. The surgical instrument of claim 5, wherein each tip includes a base portion, wherein the tines of each tip extend from the base portion.

7. The surgical instrument of claim 6, wherein the base portion of each tip includes a surface, at least a portion of which complements at least a portion of a surface of a base portion of the other tip.

8. The surgical instrument of claim 7, wherein the complementary surfaces of the base portion are continuous with the complementary surface of at least one tine of each tip.

9. The surgical instrument of claim 8, wherein the continuous complementary surfaces of the tips partition the remaining portion of the base of each tip when the complementary surfaces of the tips are in contact with each other.

10. The surgical instrument of claim 1, further including a forceps portion.

11. The surgical instrument of claim 10, wherein the forceps portion is a nonparallel-action forceps.

12. The surgical instrument of claim 10, wherein the forceps portion is a parallel-action forceps.

13. The surgical instrument of claim 12, wherein at least one of the tips is releasable from the forceps portion.

14. The surgical instrument of claim 13, wherein at least one of the tips is releasable by actuation of a spring-loaded clip that releasably couples the tip to the forceps portion.

15. The surgical instrument of claim 14, wherein a major axis of the tines extends at an oblique angle to a major axis of the forceps portion.

16. The surgical instrument of claim 15, wherein each of the recesses is chamfered and has a major axis essentially parallel to a major axis of the tines of the clip.

17. The surgical instrument of claim 16, wherein the recesses chamfered and are opposed to each other when the tips are coupled to the forceps portion.

18. The surgical instrument of claim 17, wherein the stop of at least one tip includes a chamfered surface.

19. A surgical instrument, comprising:
    a pair of forceps having a pair of distal tips configured to seat a core of an artificial disc implant therebetween, each tip having
        a base portion with a continuous concave surface defining a stop surface configured to limit proximal movement of a core implant seated between the pair of tips,
        a pair of tines extending distally from opposed ends of the stop surface, and
        a recess formed in the base portion,
    wherein the recesses in the tips face each other and are opposed to one another such that the recesses define a space that allows access to a space between the tines,
    wherein facing planar surfaces of the base portions do not contact one another when complementary surfaces of the pair of tines on one of the tips contact complementary surfaces of the pair of tines on the other one of the pair of tips, and
    wherein the recesses are formed in the facing planar surfaces and extend in a proximal to distal direction along partial lengths thereof such that the recesses extend from proximal-most ends of the surfaces and terminate proximal to the stop surfaces.

* * * * *